US005656267A

United States Patent [19]
Sagen et al.

[11] Patent Number: 5,656,267
[45] Date of Patent: Aug. 12, 1997

[54] IMPLANTABLE CELLS THAT ALLEVIATE CHRONIC PAIN IN HUMANS

[76] Inventors: Jacqueline Sagen, 2509 W. Farwell, Chicago, Ill. 60645; George Demetrios Pappas, 506 W. Roscoe, Chicago, Ill. 60657

[21] Appl. No.: 379,790

[22] Filed: Jan. 27, 1995

Related U.S. Application Data

[63] Continuation of Ser. No. 88,732, Jul. 8, 1993, abandoned, which is a continuation of Ser. No. 748,438, Aug. 22, 1991, abandoned.

[51] Int. Cl.$^6$ .................. C12N 15/00; A61K 35/30; A61K 48/00; A61F 2/66
[52] U.S. Cl. .................. 424/93.21; 424/563; 424/570; 424/520; 514/44; 604/49
[58] Field of Search .................. 514/44, 2, 85; 424/93.21, 563, 520, 521, 570; 435/172.3, 240.1, 240.2, 320.1; 800/2

[56] References Cited

U.S. PATENT DOCUMENTS 4,753,635  6/1988  Sagen et al. .................. 604/49

OTHER PUBLICATIONS

———Pain, Supplement 3, 1986. "Pain," The Intl. Assoc. for the Study of Pain. pp. S3–S4.
Aerbischer, et al., Abstract Cell Transplant. 3(3):229 (1994).
Andrews, P.W. *Dev. Biol.* 103: 285–293 (1984), copy attached as Exhibit 22 to Amendment and Response under Rule 111 filed Jun. 20, 1996).
Bonica, J., Chapter 8, The management of Pain, eds. Chapman & Fortis, Lea & Fibiger pp. 180–191 (1990).
Comb, et al., *EMBO J.* 4(12): 3115–3122 (1985) (copy attached as Exhibit 19 to Amendment and Response under Rule 111 filed Jun. 20, 1996).
Cullen, B.R., "Use of eukaryotic expression technology in the functional analysis of cloned genes", pp. 684–704 in Berger, S.L. & Kimmel, A.R., *Guide to Molecular Cloning Techniques,* Academic Press, New York (1987) (attached as Exhibit 18 to Amendment and Response under Rule 111 filed Jun.20, 1996).
Czech et al., *Prog. Neurobiology* 46: 507–529 (1995) (copy attached as Exhibit 28 to Amendment and Response under Rule 111 filed Jun. 20, 1996).
Flaris et al., *Lab Invest.* 62(4): 493–497 (Apr. 1990).
Maniatis et al., *Molecular Cloning. A Laboratory Manual,* Cold Spring Harbor (1982), (pp. i–x attached as Exhibit 16 to Amendment and Response under Rule 111 filed Jun. 20, 1996).
Lazorthes, Y., et al., *Acta Neurochir.* [Suppl. ] 64:97–100 (1995) (copy attached as Exhibit 31 to Amendment and Response under Rule 111 filed Jun. 20, 1996).
Lundberg et al., *Pro. Nat. Acad. Sci. USA* 76(8):4079–4083 (Aug. 1979).
Noël, G. et al., *J. Neurochemistry,* 52: 1050–1057 (1989) (copy attached as Exhibit 23 to Amendment and Response under Rule 111 filed Jun. 20, 1996).

Orrison, W.W., Jr., *Introduction to Neuroimaging,* Little–Brown, Boston (1989) pp. 293–313, copy attached as Exhibit 26 to Amendment and Response under Rule 111 filed Jun. 20, 1996).
Ortega et al., Abstract, III Intl Symp. on Neural Transplant. p. 26 (198?).
Pappas et al., Abstract. Fifth Intl. Symp. on Chromaffin Cell Biol. p. 60 (1989 ).
Sagen et al., *Ann. N.Y. Acad. Sci.* 495:306–333 (1987).
Pappas et al., Abstract, III INtl Symp. on Neural Transplant. p. 25 (198?).
Sagen et al., *Experimental Neurology* 102: 290–297 (1988) (copy attached as Exhibit 24 to Amendment and Response under Rule 111 filed Jun. 20, 1996).
Sagen et al., Abstract. Fifth Intl Symp. on Chromaffin Cell Biol. p. 115 (1989).
Sagen, et al., Abstract 51.
Sagen et al., *Cell Transplantation* 2: 259–266 (1993) (copy attached as Exhibit 30 to Amendment and Response under Rule 111 filed Jun. 20, 1996).
Sagen et al., *Brain Res.* 502: 1–10 (1989).
Sagen et al., *Pain* 42: 69–79 (1990).
Sambrook et al., *Molecular Cloning. A Laboratory Manual 2d,* Cold Spring Harbor (1989) (pp. 16.2–16.36 attached as Exhibit 17 to Amendment and Response under Rule 111 filed Jun.20, 1996).
Sardet, C. et al., *Cell* 56:271–280 (1989) (copy attached as Exhibit 20 to Amendment and Response under Rule 111 filed Jun. 20, 1996).
Unsicker, K., *Experimental Neurology,* 123: 167–173 (1993) (copy attached as Exhibit 32 to Amendment and Response under Rule 111 filed 20, 1996).
Unsicker, et al., *Int. J. Devl. Neuroscience,* 10: 171–179 (1992) (copy attached as Exhibit 33 to Amendment and Response under Rule 111 filed Jun. 20, 1996).
Vaquero et al., *The Lancet,* 1315 (1988) (copy attached as Exhibit 9 to Amendment and Response under Rule 111 filed Jun. 20, 1996).
Wang, et al., Abstract, Soc. Neurosci. 14:1005 (1988).
Winnie et al., *Anesthesiology* 79: 644–653 (1993) (copy attached as Exhibit 29 to Amendment and Response under Rule 111 filed Jun. 20, 1996).
Yaksh, T.L. The central pharmacology of Pain States in *Basic Mechanisms of Pain and Pain Control* .
Sagen et al., Ann. N.Y. Acad. Sci., 495, 1987, 306–333.
Vaquero et al., The Lancet, Dec. 3, 1988, 1315.
Czech et al., Prog. Neurobiology, vol. 46, 1995, 507–529.

*Primary Examiner*—Jacqueline M. Stone
*Assistant Examiner*—Andrew Milne
*Attorney, Agent, or Firm*—Olson & Hierl, Ltd.

[57] ABSTRACT

This invention provides a method of alleviating chronic pain in humans. Viable, implantable cells are selected which release neuroactive substances that reduce chronic pain. The cells are cultured to improve their viability, and administered into a region of the central nervous system of a patient who is suffering from chronic pain. The cells continue to secrete the neuroactive substances within the patient without exogenous stimulation. Suitable implantable cells include adrenal medullary tissue cells, chromaffin cells or genetically engineered cells.

42 Claims, 8 Drawing Sheets

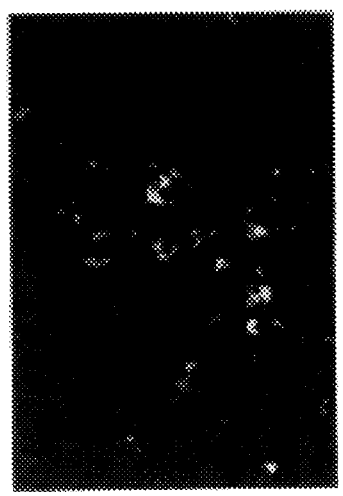 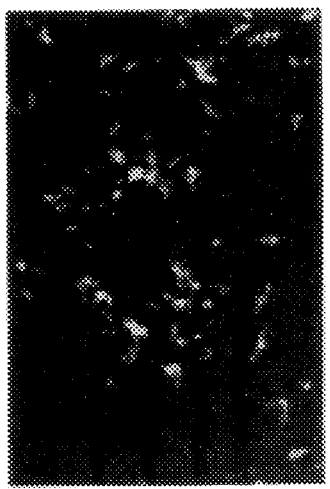 
DAY 1
FIG. 5A
DAY 3
FIG. 5B
DAY 7
FIG. 5C

DAY 14

DAY 21

DAY 35

IMPLANTABLE CELLS THAT ALLEVIATE CHRONIC PAIN IN HUMANS

This is a continuation of application Ser. No. 08/088,732 filed Jul. 8, 1993 (now abandoned) which in turn is a continuation of Ser. No. 07/748,438 filed Aug. 22, 1991, (now abandoned).

The present invention is related to producing analgesia or reducing pain sensitivity. More, particularly, the present invention is related to alleviating chronic pain by implanting living cells which secrete neuroactive substances that reduce or eliminate chronic pain without exogenous administration of an agonist, drug, stimulant or the like to activate or stimulate the implanted cells to alleviate chronic pain.

U.S. Pat. No. 4,753,635 to Sagen et al describes a method of inducing analgesia where exogenous administration of an agonist is required. Sagen et al, 1990 (Pain, 42:69–78) reported experiments where adrenal medullary implants in the rat spinal cord appeared to reduce chronic pain sensation although vocalization did not subside without nicotine injection. Because of the fundamental limitation that a subjective human feeling and condition, such as chronic pain, cannot be equated with any degree of certainty with an animal model, no matter how sophisticated, a need existed for a clinical study to determine whether chronic pain can be alleviated in humans by cellular implants that secrete neuroactive substances without requiring exogenous administration of stimulants and the like to release antinociceptive substances. Such a human study had not heretofore been known or described.

SUMMARY OF INVENTION

It is, therefore, an object of the present invention to provide implantable living cells, either isolated from other tissues or recombinantly made, so that when said cells are implanted in humans, chronic severe pain is alleviated without exogenous administration of any chemical agent to the patient to stimulate the implanted cells to release increased amounts of neuroactive substances that subside pain sensation.

It is another object of the present invention to provide a method of alleviating chronic pain without exogenously introducing or administering any inanimate substance, such as a chemical agent, drug, agonist or stimulant and the like, to the patient suffering from intolerable chronic pain, in order to stimulate the implanted cells to release antinociceptive substances.

Other objects and advantages will become evident from the following detailed description of the invention.

BRIEF DESCRIPTION OF THE DRAWINGS

These and other objects, features and many of the attendant advantages of the invention will be better understood upon a reading of the following detailed description when considered in connection with the accompanying drawings wherein.

(b) shows narcotic intake of Patient 1 (daily intake of Dilaudid tablets, 2 mg) before (at time 0) and at several intervals following the transplant.

(c) shows met-enkephalin levels (pg/ml) of Patient 1 in CSF obtained via lumbar puncture before, 1 week, and 4 weeks following the transplant.

Figure 2A:
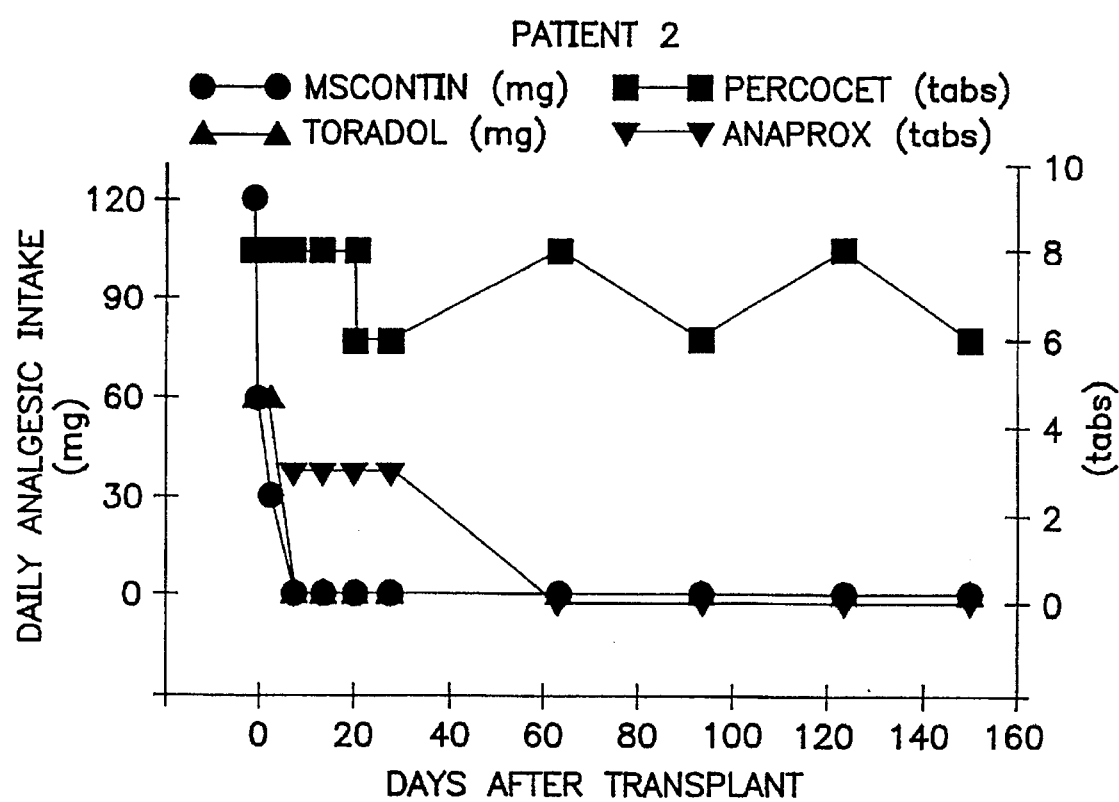

FIG. 2(a) shows narcotic intake (mg Mscontin and Toradol, left ordinate, and Percocet and Anaprox, right ordinate) before (at day 0) and several intervals following the transplant, for Patient 2.

(b) Pain scores of Patient 2 using the Visual Analog Scale (VAS) before (at day 0) and at several intervals following the transplant.

(c) Daily activity of Patient 2 (number of hours out of bed) before (at day 0) and at several intervals following the transplant.

Figure 3A:
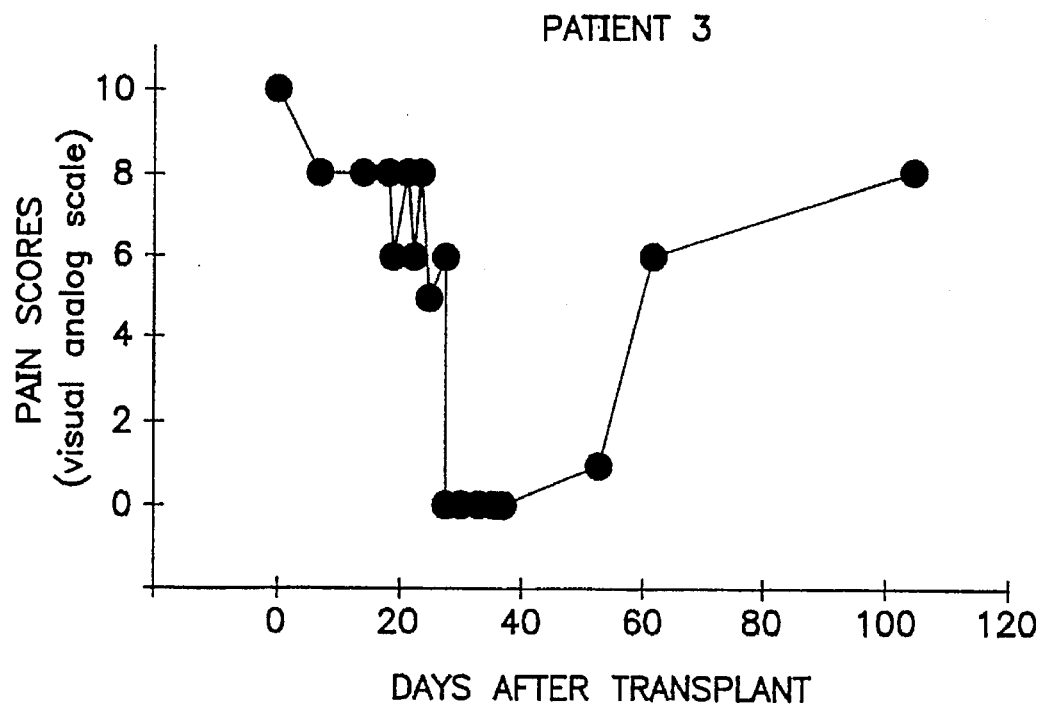
Figure 3B:
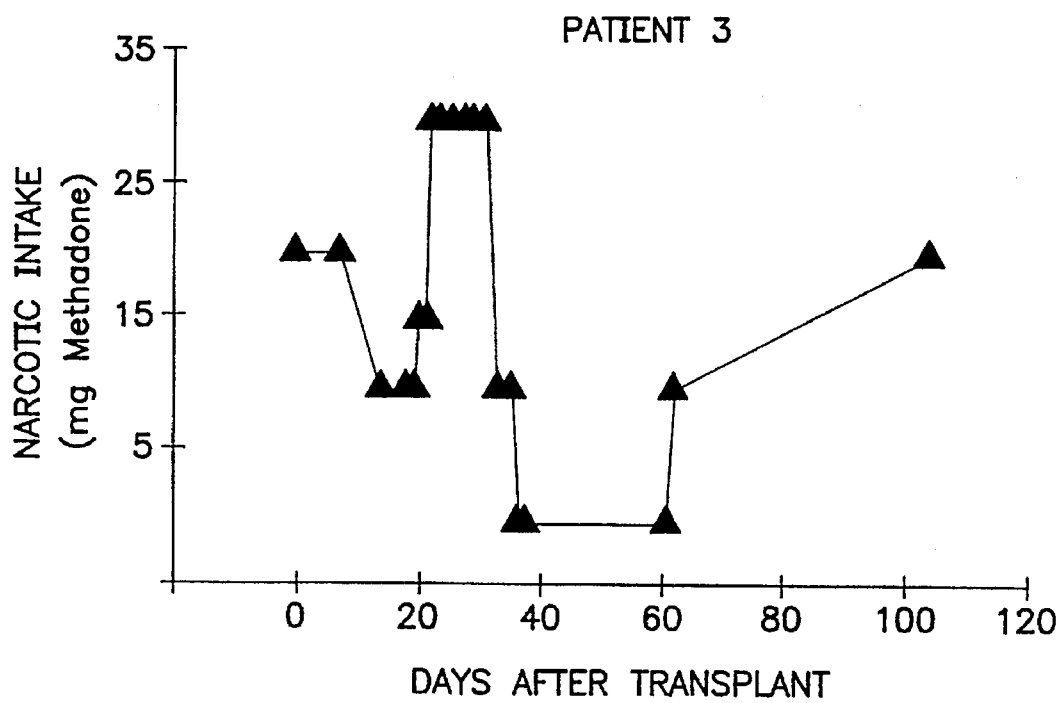

FIG. 3 (a) shows pain scores of Patient 3 using the VAS before (at day 0) and at several intervals following the transplant.

(b) shows narcotic intake (mg Methadone) of Patient 3 before (at day 0) and at several intervals following the transplant.

Figure 4A:
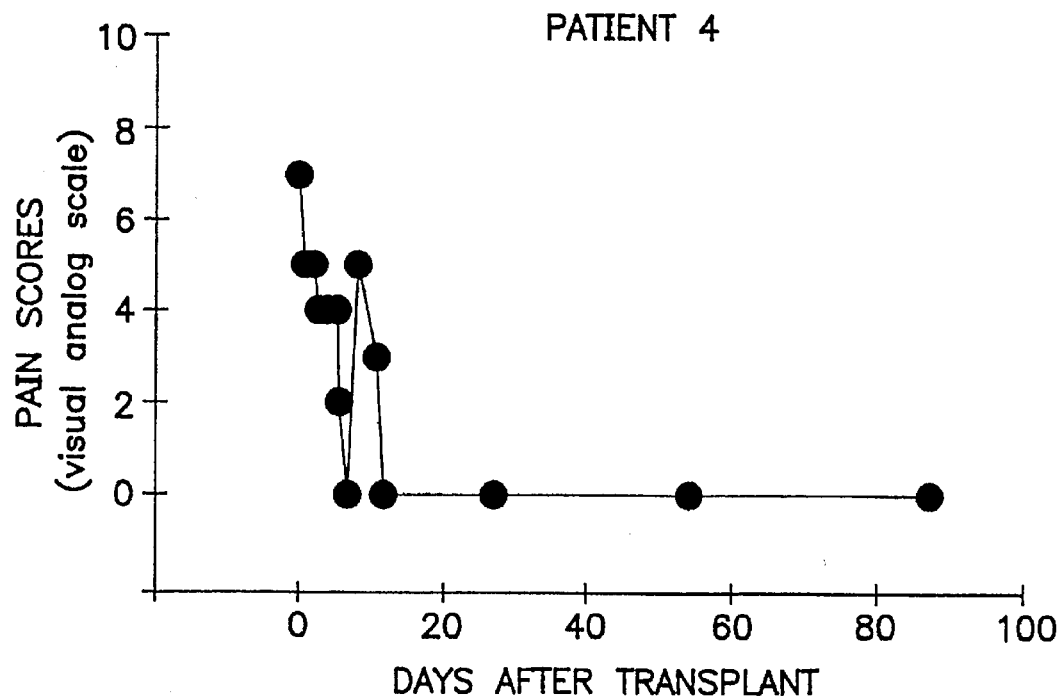

FIG. 4 (a) shows pain scores of Patient 4 using the VAS before (at day 0) and at several intervals following the transplant.

(b) Patient 4 narcotic intake (mg Mscontin) before (at day 0) and at several intervals following the transplant.

(c) Patient 4 CSF levels of norepinephrine (NE, left ordinate), epinephrine (EPI, right ordinate), Dopamine (DA, right ordinate), and met-enkephalin (MET, right ordinate), taken via lumbar puncture before, 1 week, and 8 weeks following the transplant.

Figure 5D:
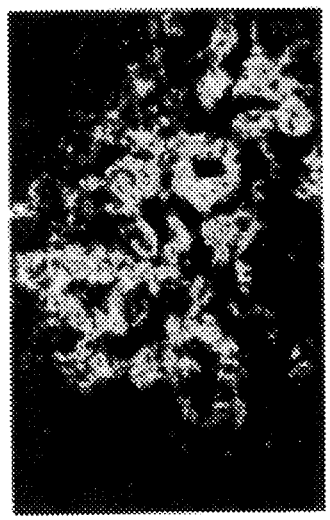
Figure 5E:
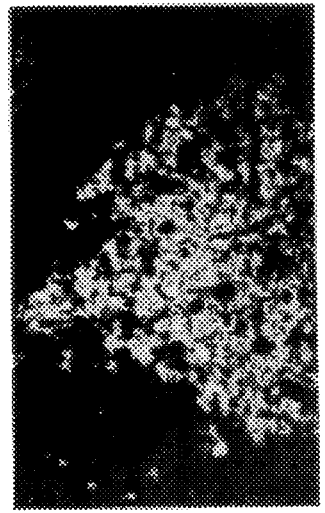
Figure 5F:
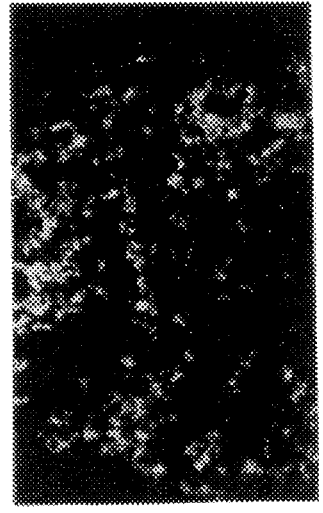

FIG. 5 shows human adrenal medullary tissue maintained in culture for 1–35 days following harvesting from donor glands. The chromaffin cells in the explants are stained with an antibody to tyrosine hydroxylase.

DETAILED DESCRIPTION OF THE INVENTION

The above and various other objects and advantages of the present invention are achieved by making genetically engineered permanent cell lines that release neuroactive substances in chronic pain condition in humans, without the necessity of exogenously stimulating or activating the genetically engineered cells to release neuroactive substances. Examples of such neuroactive substances are neuropeptides, neurotransmitters, opioids and the like.

Another aspect of the present invention provides a method of relieving pain that comprises the step of introducing in a nociceptor region of the central nervous system of a patient suffering from intolerable chronic pain, such cells or tissues that release effective amount of antinociceptive substances to alleviate the chronic pain without administering any exogenous agent or stimulant to said patient in order to stimulate the implanted cells. It is noted that analgesic drugs, such as codeine, morphine, aspirin, tylenol, methadone, mscontin and the like are not considered herein as stimulants or activating agents. Typical examples of a stimulant or an activating agent in context of the present disclosure are nicotine and other muscarinic agonists and the like.

Unless mentioned or defined otherwise, all scientific or technical terms used herein have the same meaning as generally understood by one of ordinary skill in the art and the methods and materials used and/or contemplated herein are standard, conventional techniques or methodologies well known in the art. Although any similar or equivalent methods and materials can be conveniently adopted in the practice or testing of the invention disclosed herein, the preferred methods and materials are now described, these methods and materials being only illustrative and not limiting.

The term "isolated" cells as used herein means those implantable cells which are obtained by separation from the naturally occurring tissues or from a culture of genetically engineered cells. A characteristic of these cells is that they are substantially homogeneous or uniform in their properties. Isolated cells alleviate chronic pain when implanted in a nociceptor region of the central nervous system of a patient suffering from chronic pain without exogenous stimulation of the implanted cells. Chronic pain in humans can be alleviated by the step of implanting these isolated cells in a nociceptor region of the central nervous system of a patient suffering from chronic pain.

MATERIALS AND METHODS

A. Human adrenal medullary tissue allografts.

Adrenal medullary tissue for transplantation was obtained from the Regional Organ Donor Branch of Illinois from donors who had undergone brain death and were being ventilated mechanically. Since the adrenal glands are routinely removed with the kidneys used for transplantation, they are screened for HIV, Herpes viruses, etc. The adrenal glands were transported to the laboratory in ice-cold sterile saline. The glands were washed in Locke's buffer containing kanamycin, penicillin-streptomycin, and fungizone, and adrenal medullary tissue was dissected free of cortical tissue as much as possible. Small pieces of adrenal medullary tissue (0.5–2.0 mm) were placed in tissue culture plates by seeding in small volumes of 1:1 DMEM:F12 media for several hours until they attached. Additional media was added as necessary. The adrenal medullary tissue was maintained at 37° C., 5% $CO_2$ in a dedicated tissue culture incubator until transplanted. Tests performed in our laboratory have indicated that human adrenal medullary tissue can be maintained in culture for at least 30 days following removal from the donor and short-term maintenance of adrenal medullary tissue in culture (7–21 days) improves tissue viability with increased production of both catecholamine and opioid peptide (FIG. 5). Without being bound to any specific theory, it is postulated that this may be due to the time required for recovery from tissue trauma following dissection procedures. In addition, maintenance in explant culture may allow for the migration of passenger leukocytes out of the explanted tissue, reducing the potential for immunologic reaction when transplanted to an allogeneic host.

B. Biochemical and morphological analyses.

Prior to transplantation, tissue viability was assessed using immunocytochemistry and biochemical assays. For immunocytochemical analysis, some tissue pieces were fixed in 4% paraformaldehyde in 0.1 M phosphate buffer and then placed in 20% sucrose for cryopreservation. Twenty micron sections were cut on a Hacker-Bright cryostat, mounted on gelatinized slides, incubated in phosphate-buffered saline (PBS) containing 1% normal goat serum, and placed in primary antibody solution overnight at 4° C. These included catecholamine-synthetic enzymes tyrosine hydroxylase (diluted 1:500, Incstar), dopamine-β-hydroxylase (diluted 1:1000, Eugene Tech), opioid peptides met- and leuenkephalin (diluted 1:500, Incstar), and chromogranin (diluted 1:500, Incstar). In addition to producing catecholamines and opioid peptides, chromaffin cells produce other neuropeptides, particularly neuropeptide Y which has been implicated in the production of analgesia. Following several washes, a fluorescein-or rhodamine-linked secondary antibody were applied for 1 hour at room temperature (22°–24° C.). The sections were washed, coverslipped with Fluoromount, and observed in a Zeiss Axiophot fluorescence microscope. In addition to immunocytochemistry, some tissue pieces were fixed for electron microscopy by the addition of 2.5% glutaraldehyde in the fix solution, dehydrated in a graded ethanol series, and embedded in Epon. Thin sections were observed in a JEOL 100S electron microscope to analyze tissue morphology prior to transplantation.

Biochemical analysis was also performed prior to transplantation. Both catecholamine and opioid peptide release from some of the tissue pieces was determined. Catecholamine samples were assayed by high performance liquid chromatography (HPLC) with electrochemical detection. Samples were prepared for HPLC using the alumina extraction method. Catecholamines absorbed to acid-washed alumina at pH 8.6 were eluted with 0.1 N perchloric acid. To calculate recovery, dihydroxybenzylamine (DHBA) was added to each tube as an internal standard. Catecholamine sample concentrations were calculated using a Waters Baseline 810 system following separation over a Waters Resolve $C_{18}$ column (flow rate 1.0 ml/min). The HPLC mobile phase for catecholamines comprises 0.07 M $NaH_2PO_4$, 0.02 mM octyl sodium sulfate, 0.1 mM EDTA, 8% methanol, pH 4.8.

Peptides were assayed by radioimmunoassay (RIA). We have routinely used the met-enkephalin antibody supplied by Incstar to assay levels of met-enkephalin in both tissue culture and spinal cord CSF samples (Kemmler and Sagen, 1989; Soc. Neurosci. 15:1243; Sagen and Pappas, 1990 Soc. Neurosci. 16:835.). Samples were lyophilized a and reconstituted in 100 μl assay buffer (phosphate buffered saline with 0.01% bovine serum albumin). Serially diluted met-enkephalin standards (Bachem) were used for generation of the standard curve. Non-specific binding tubes contained trace ($^{125}$I-met-enkephalin) and assay buffer only. Total binding is determined in the absence of cold metenkephalin. The reaction is stopped using IgGsorb (Enzyme Center), and the bound fraction is pelleted for counting with a gamma counter. The sensitivity limit for this assay is 0.5 pg.

Both basal release of catecholamines and opioid peptides, and release following stimulation with high K+ or nicotine (61 μM) were determined for tissue samples. Samples collected for catecholamine assays were protected with antioxidants (0.1 ml 4% L-cysteine, 0.01 ml 5% sodium metabisulfite, and 0.05 ml EDTA, per 1 ml sample). Samples for peptide assays were collected in 0.05 μg/ml bacitracin and 0.1 mg/ml bovine serum albumin, to inhibit peptidase activity and reduce non-specific binding, respectively.

Cerebrospinal fluid samples from the patients were also assayed for opioid peptides and catecholamines using similar techniques. One ml CSF samples were collected in tubes as described above, frozen, lyophilized and stored at −70° C. until assayed.

C. Transplantation procedures

Only terminal patients with intractable cancer pain from a well known organic lesion were selected for this study. The patient's life expectancy was determined to be 3–6 months. Selection was based on the patient's increasing demand for narcotics which did not satisfactorily control their pain. Patients with immunological disorders, seizure disorders, or major organ dysfunction were excluded from the study. Preoperative evaluation required that coagulation parameters were within normal limits. Details of the procedure and potential risks were openly discussed with the patient and involved relatives prior to signing a consent form.

On the day of transplantation, the cellular mass (tissue) was checked for contamination including mycoplasma using a Hoescht stain. The tissue pieces were scraped from the plate, washed and centrifuged several times in sterile Locke buffer to remove all media, and resuspended in small volumes of buffer (<3 cc). For implantation, the patient was placed in the lateral flexed position. The lumbar area was cleaned, prepped, and draped for sterile procedures. Lumbar puncture was accomplished with a 14-gauge Tuohy or Quincke needle. Six to ten cc of cerebrospinal fluid were withdrawn for biochemical assays as described above, and for cytology (including cell count, culture, total protein and glucose). An additional 3 cc of CSF was withdrawn and reserved for flushing the spinal needle following implantation of tissue. Tissue was injected into the subarachnoid space, followed by the CSF flush. The spinal needle was removed, and a bandage put in place.

Following removal of the needle, the patient was kept supine for several hours, during which time several liters of fluid was administered intravenously to protect against development of a post-dural puncture headache. As prophylaxis against infection, antibiotic Vancomycin and Gentamycin were administered intravenously.

D. Patient follow-up.

Pain was assessed in the patients both prior to and following implantation using the Visual analog Pain Score (at least twice weekly), monitoring daily doses of narcotics (analgesics consumed over 24 hours), and interviewing patients and relatives regarding daily physical activity, sleep and eating patterns, etc. Interviews were conducted by a neutral observer. The patient was contacted by telephone 24 hours following discharge from the hospital and then approximately twice a week for assessment of pain, activity, sleep and eating patterns, and adjustment of dose of analgesic drugs.

Diagnostic lumbar punctures were performed when possible with a 22 gauge needle at one week, one month, two months, four months, and six months following the implantation for cytology and biochemical analyses as described above.

E. Clinical Trials

EXAMPLE 1

Patient 1

Patient 1 was a 61 year old female with a 6 year history of carcinoma of the colon. She had multiple abdominal surgical procedures, as well as a colostomy and ureteral diversion. She had full course radiation therapy, as well as chemotherapy with 5-FU, which had been discontinued. On a clinical and radiologic basis, she was found to have involvement of the lumbosacral plexus on both sides. Her back pain and lower extremity pain had become intractable, despite escalating doses of narcotics and phenothiazides. Her verbal and visual analog pain scores were in the range of 8–9 (10 being the worst possible). Descriptively, the pain was described by the patient as of a most severe nature. She was taking 6–8 Dilaudid tablets daily (1 every 4 hours and 1 at night to sleep).

The patient received a transplant of adrenal medullary tissue harvested from an accident victim (obtained via the Regional Organ Donor Branch of Illinois). The tissue was tested for viability using immunocytochemistry and biochemical assays for opioid peptides and catecholamines prior to transplantation. Prior to implantation, 6 cc of CSF were removed for cytology and biochemical assays. One cc of adrenal medullary tissue was transplanted via a lumbar puncture at the L2-L3 interspace with an 18 ga needle. The patient received the immunosuppressant Cyclosporine A (500 mg) one day prior to the procedure. She was instructed to continue with daily Cyclosporine for 2 weeks, but discontinued this medication after 5 days due to complaints of nausea.

Pain levels were assessed using the Visual Analog scale and daily narcotic intake was monitored following the procedure. Two additional lumbar punctures were taken for biochemical assays, at one week and one month following the procedure.

Figure 1A:
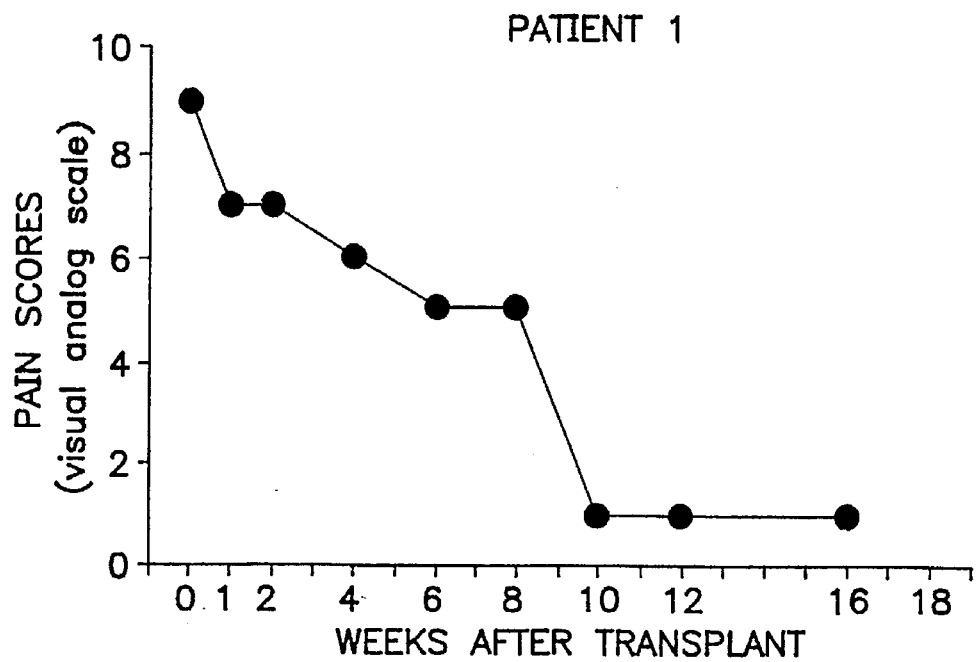
FIG. 1(a) shows the pain scores of Patient 1 using Visual Analog Scale (0–10, 10 being the worst pain possible, 0 being no pain). Pain scores were taken before (at 0) and at several intervals following the transplant.
Figure 1B:
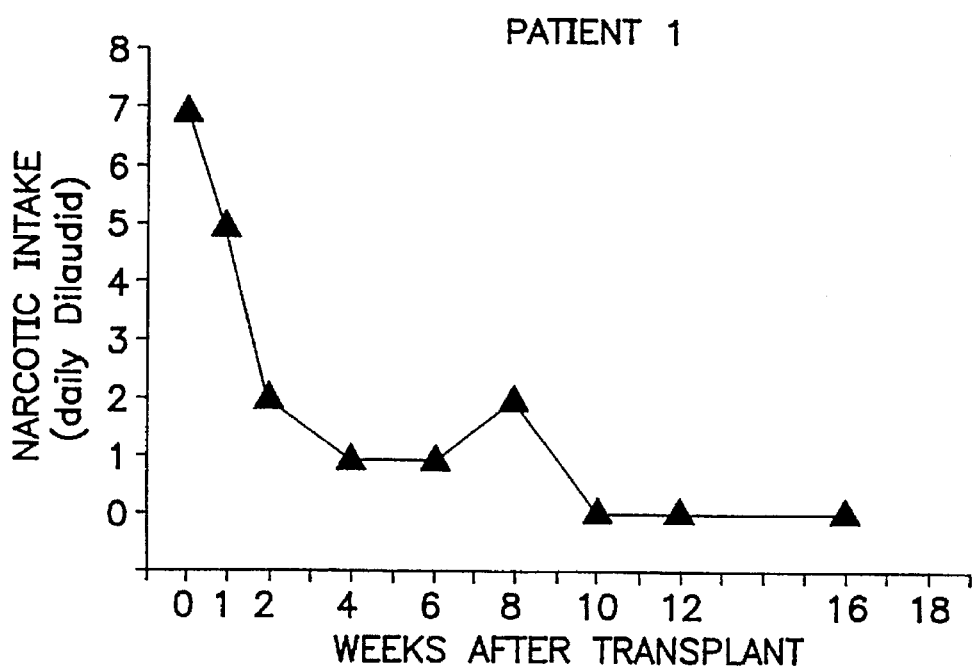
Figure 1C:
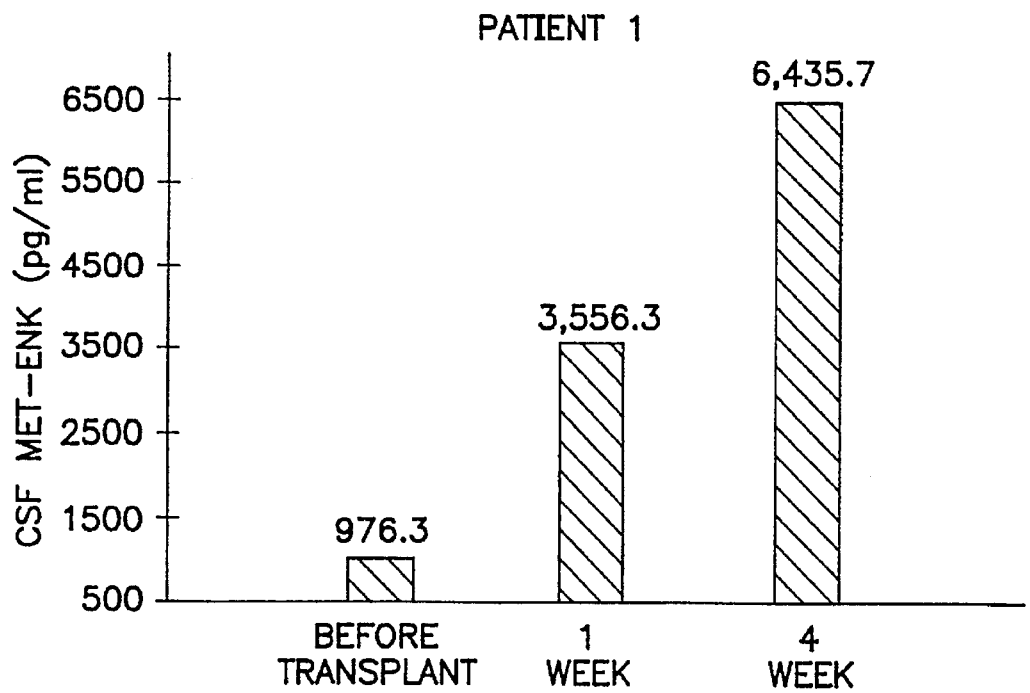

The results are presented graphically. FIG. 1A shows the changes in pain scores following the transplantation. (Pain scores are plotted on a scale of 1–10, 10 being the most severe). Pain scores were reduced to moderate levels during the first month after the procedure. In addition, narcotic intake was markedly reduced from 7–8 Dilaudid daily to 1–2 during this period (FIG. 1B). This improvement continued during the remainder of the patient's life (approximately 4½ months following the procedure). In the last 2 months of life, the patient claimed that pain was no longer a problem of significance. FIG. 1C shows the changes in CSF met-enkephalin levels which were increased by approximately 3-fold one week following the procedure and 6-fold at one month following transplantation.

Death occurred 4½ months due to general debilitation and gastrointestinal involvement secondary to metastatic colonic carcinoma. Autopsy was refused.

EXAMPLE 2

Patient 2

Patient 2 was a 69 year old white male who developed a carcinoma of the colon, first diagnosed 4 years ago. He underwent a colon resection with no colostomy at that time. He did well for approximately two years, at which time he developed pain in the pubic area, apparently due to metastasis, for which he underwent 45 radiation treatments. Following initial but transient amelioration, his pain returned and became progressively worse and more resistant to analgesic medications. The patient developed an acute bowel obstruction due to further metastasis, and this required a colostomy. In spite of this surgery, the patient's pain continued to increase. CT scan, bone scan, and ultimately a biopsy revealed metastatic carcinoma in the sacrum, the region of his worst pain. The pain was highly "position dependent" in that he was in mild to moderate pain if he remained supine in bed. However, if he attempted to sit up, the pain became unbearable within a very short period of time. Since he no longer obtained relief from systemic narcotics, an indwelling catheter was implanted to deliver narcotics systemically. However, after a week the catheter became infected and had to be removed.

Figure 2B:
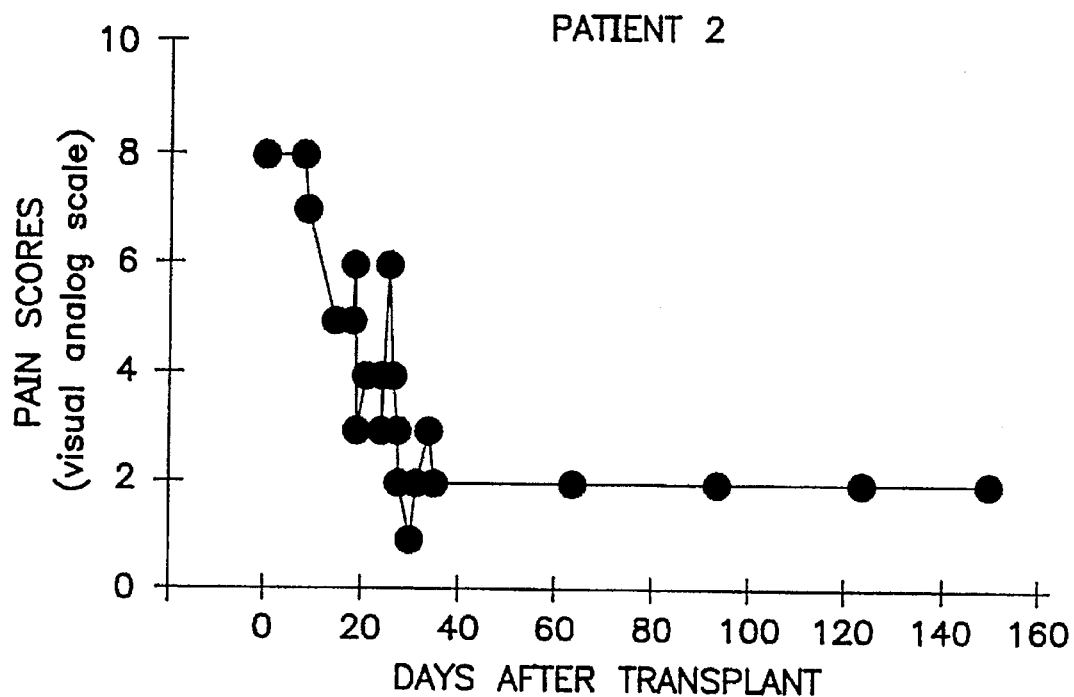
Figure 2C:
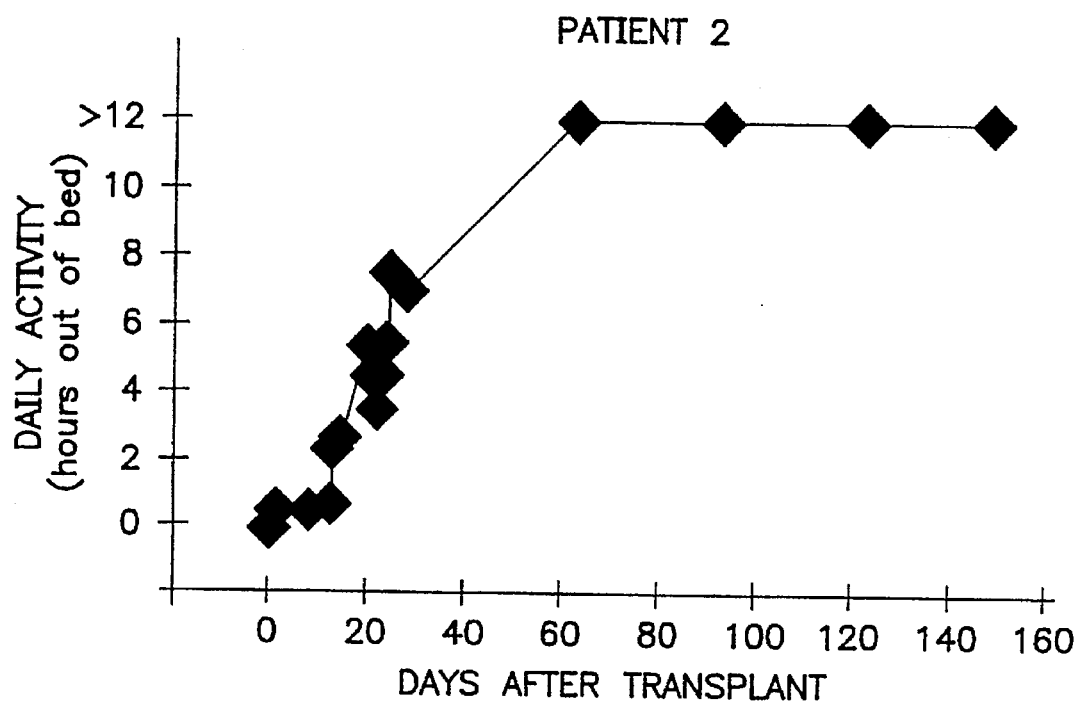

For transplantation, the patient was placed in the left lateral decubitus position, and a 14-gauge Tuohy needle was inserted into the subarachnoid space. Following the aspiration of sufficient CSF for the necessary biochemical assays, adrenal medullary tissue was injected as described above. He received Cyclosporine A (500 mg) one day prior to and for 2 weeks following the transplantation. Following an uneventful recovery, he was discharged on the following day. Over the following month, though the patient needed some Percocet (FIG. 2A), the pain scores were significantly reduced from 8–9 to 2–3 (FIG. 2B), and the patient spent progressively increasing periods of time out of bed, sitting in a recliner, something that was previously impossible even with Percocet regimen. Since that time, the patient has been able to spend most of the day out of bed, either walking or sitting, and has resumed near normal daily activities (FIG. 2C). At 6 months after the transplant, the patient was still pain free.

EXAMPLE 3

Patient 3

Patient 3 was a 49 year old female who developed carcinoma of the left breast 3 years ago, for which she underwent a left mastectomy followed by chemotherapy. Two years later, she began to complain of pain in her low back, right hip, and buttocks. A CT scan of the thoracic spine revealed metastasis to the second and third thoracic vertebrae with evidence of cord compression, so she underwent a course of radiation therapy applied to this area. Later that year an MRI scan of the lumbosacral spine showed metastasis to the second and third lumbar vertebrae and bulging disc at the L4-L5 level. Surgical intervention was not recommended, and the patient received further radiation therapy. The patient complained of severe low back pain from T12 through L5, which radiated to her right hip. She was becoming unresponsive to narcotic analgesics, and was referred to the Pain Control Center for adrenal medullary transplant. The night before the procedure she was given Cyclosporine A (10 mg/kg), and the following morning she was given prophylactic antibiotics. To implant the tissue, the patient was placed in the left lateral decubitus position, the back prepared and draped, and a 14 gauge Tuohy needle was inserted into the subarachnoid space. Following aspiration of some clear, CSF, it became difficult to obtain more fluid, and the needle was withdrawn and the subarachnoid space re-entered. Although some blood was found in the CSF, the adrenal medullary tissue was implanted and the needle was removed. The following day, following an uneventful recovery from the procedure, the patient was discharged and instructed to continue the Cyclosporine A (10 mg/kg daily) for two weeks.

During the following month, the patient's pain scores and narcotic intake were progressively reduced (FIG. 3A, B). At one to two months following the transplant, the patient's back and right hip pain were resolved. However, the patient complained of progressive weakness on her lower extremities with increasing difficulty in ambulation. A CAT scan/myelogram reveled a spinal block at the level of her metastasis at T2. Since this time, here pain has returned, possibly due to spinal compression or limited CSF perfusion of the transplant. Further sampling of CSF has not been done at the request of the Neurosurgical Service.

EXAMPLE 4

Patient 4

Patient 4 was a 52 year old Hispanic male who was diagnosed with colon cancer in 1987. At that time he underwent an abdominal-peritoneal resection followed by chemotherapy and radiation therapy. A subsequent perirectal recurrence required surgical excision, after which he did well until 1990 when he developed pain in the sacral area radiating to the lower abdomen in the suprapubic region. The pain was described at first as a dull ache but subsequently became quite severe, and management as an outpatient on oral narcotics failed to control his pain. On hospital admission, X-rays and CAT scans revealed pulmonary metastasis and diffuse abdominal lymph node enlargement. In addition, a CAT scan indicated left ureteral obstruction, for which a left ureteral stent was placed. When the patient became unresponsive to increasing doses of narcotic analgesics, the Pain Control Center was contacted concerning the possibility of a subarachnoid adrenal medullary transplant. On the evening before the procedure, the patient was given Cyclosporine (10 mg/kg), to be continued for 2 weeks. The following morning, he was given prophylactic antibiotics, and placed in the lateral decubitus position for the procedure. The back was prepared and draped, and a 14-gauge Tuohy needle was inserted into the subarachnoid space. The first attempt yielded clear CSF, which was collected for biochemical assays and cytology, followed by the transplantation of adrenal medullary tissue. The procedure went smoothly and the recovery was uneventful.

Figure 4B:
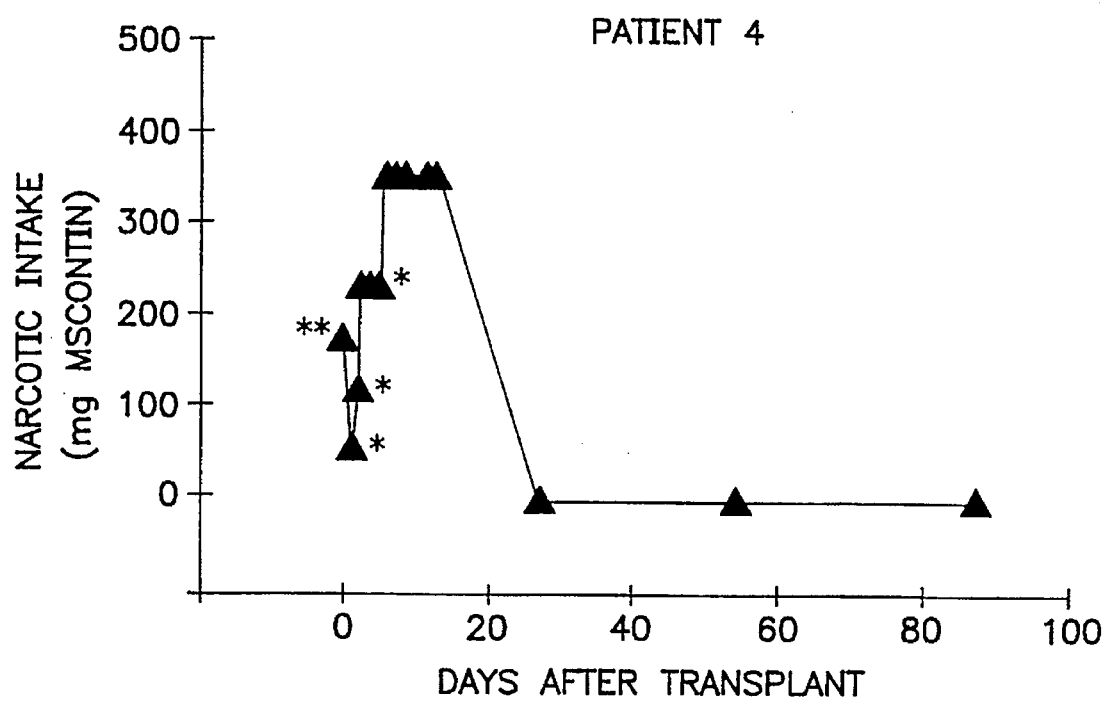
Figure 4C:
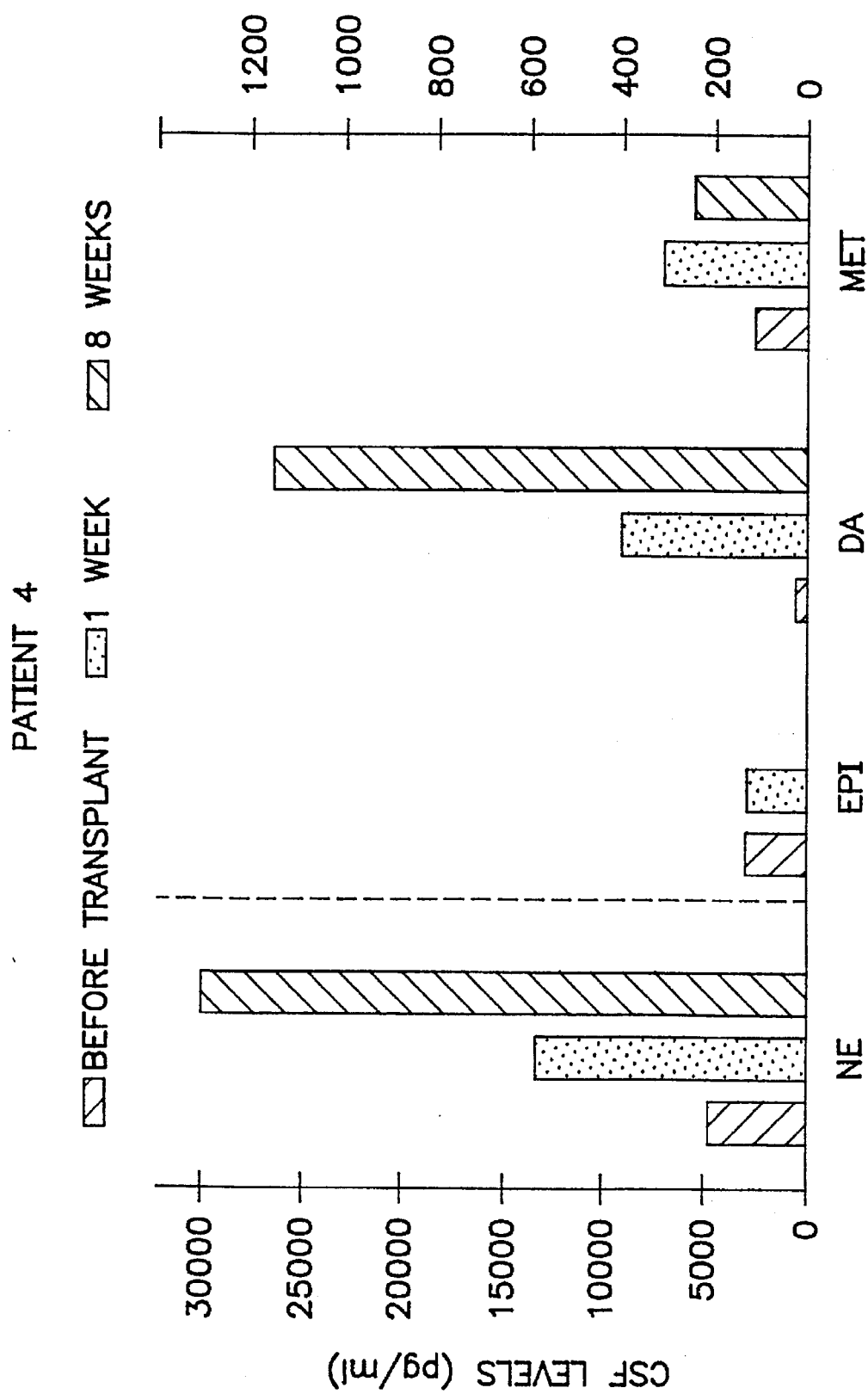

Over the ensuing week following the transplant injection, the patient's pain scores fell from 8 to 3 (FIG. 4A) and the patient's need for analgesic medications decreased concomitantly (FIG. 4B). By the time he was discharged from the hospital two weeks following the transplant, the patient was pain free and off all medications. The patient has remained pain free for at least 3 months following the procedure. Assays of spinal CSF before and 1 and 8 weeks following transplantation revealed a progressive increase in norepinephrine levels, up almost 3-fold by 1 week, and 6-fold at 8 weeks following the adrenal medullary transplant (FIG. 4C; note the scale differences for norepinephrine (NE)—left Y-axis and epinephrine (EPI), dopamine (DA), and met-enkephalin (MET)—right Y-axis). Both dopamine and met-enkephalin levels are also significantly increased following the procedure.

It is noted that tissues other than adrenal medullary chromaffin cells, such as pineal and pituitary glands can also be similarly used to alleviate pain.

Genetically engineered cells.

The success obtained with the clinical studies suggested that rather than depending on the availability and the need for careful evaluation of other complicating factors associated with human cells for implantation (such as contamination, HIV infection, etc.), genetically engineered permanent cell lines which produce high levels of neuroactive substances should be made.

EXAMPLE 5

Genetically Engineered PC12 Cells: Co-Transfection with Two Plasmids

PC12 cells (such as ATCC CRL-1721) are useful in this respect since they are derived from a rat adrenal medullary pheochromocytoma, and resemble chromaffin cells in many respects. In order to produce a genetically engineered permanent cell line useful for pain therapy, a plasmid containing, for example, the human proenkephalin gene (pHENK) is made using a co-transfection procedure with the bacterial neogene (under control, for example, of the Rous Sarcoma Virus promoter, RSV), which confers resistance to the aminoglycoside drug G418 as a dominant selectable marker. To increase the probability that a G418 resistant clone would have integrated the enkephalin gene, the pHENK plasmid is provided in 5 fold molar excess over pRSVneo.

The procedures and techniques followed for producing such genetically engineered recombinant cell lines are well known in the art and described in such publications as Maniatis, T. et al. Molecular Cloning

EXAMPLE 6

Genetically Engineered PC12 Cells: Transfection with Proenkephalin in a neo Vector A modification to A Lab. Manual, 1982, Cold Spring Harbor, N.Y. A modification to this protocol is the creation of a single plasmid that contains both the neo gene and the human enkephalin gene. New neo vectors have recently become available which contain multiple cloning sites (e.g.

pMAMneo, Clontech, Palo Alto, Calif.). The presence of both the neo gene (with the SV40 promoter) and the human enkephalin gene on the same plasmid, will prevent the isolation of G418-resistant PC12 cells which have not integrated the enkephalin gene. PC12 cells are transfected using the calcium phosphate transfection procedure followed by glycerol shock, and selected 48 hours later with the addition of G418 (800 µg/ml). Using this technique, approximately 95% of the G418-resistant clones are expected to contain the pHENK gene. Southern analysis of the DNA isolated from the clones are done to confirm the integration of pHENK in the chromosomal DNA of the clones, as well as allow for an estimation of the number of copies of the pHENK gene in each clone. The human proenkephalin gene can be differentiated from the endogenous rat proenkephalin gene in these Southern blots because the EcoRI or HindIII restriction digests of high molecular weight genomic DNA, when hybridized with a proenkephalin cDNA probe, will give different size fragments in rat and human.

To determine whether the integrated human proenkephalin gene is expressed, the total RNA isolated from the PC12/pHENK clones is analyzed by Northern analysis. The human proenkephalin mRNA can be differentiated from any low levels of endogenous rat proenkephalin mRNA by differential probes to the 5' untranslated regions of the mRNA which are not conserved between the two species. Clones which express high levels of human proenkephalin mRNA are then further analyzed for the presence and secretion of opioid peptide products.

Prior to transplantation, PC12 cells are treated with antimitotic agents mitomycin C (5 µg/ml) and 5-Bromo-2'-deoxyuridine ($10^{-5}$ M) for 48 hours to arrest cell proliferation and prevent tumor growth following transplantation. To assure that this procedure does not alter cell viability or opioid peptide production, viability testing and met-enkephalin release are determined prior to transplantation.

EXAMPLE 7

Genetically Engineered AtT-20 Cells

Another potentially useful cell line for transplantation is the mouse pituitary cell line, AtT-20 (ATCC CRL-1795), which has been transfected with the human proenkephalin gene using methods similar to those described above. These cells express proenkephalin protein and process the precursor to met-enkephalin, in addition to β-endorphin and other bioactive POMC products (Comb, M. et al., 1985. Expression of the human proenkephalin gene in mouse pituitary cells: accurate and efficient mRNA production and proteolytic processing, EMBO J. 4:3115–3122).

Of course, given the above direction and description, other permanent, recombinant cell lines can be conveniently made by a skilled artisan in this field.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A method of alleviating chronic pain in humans, comprising the steps of
    selecting viable, implantable cells which release neuroactive substances that reduce chronic pain,
    culturing the cells to improve the viability of the cells, and
    administering the cells into a region of the central nervous system of a patient who is suffering from chronic pain of nociceptive, somatic, visceral, neuropathic or central origin whereby the cells continue to secrete the neuroactive substances without exogenous stimulation within the patient.

2. The method of claim 1, wherein said region of the central nervous system is subarachnoid space.

3. The method of claim 1, wherein said neuroactive substance is chosen from the group consisting of opioid peptides, neurotransmitters and neuropeptides.

4. The method of claim 3, wherein said neuroactive substance is an opioid peptide.

5. The method of claim 4, wherein said opioid peptide is met-enkephalin.

6. The method of claim 3, wherein said neuroactive substance is a neurotransmitter.

7. The method of claim 6, wherein said neurotransmitter is a catecholamine.

8. The method of claim 1, wherein said implantable cells are chromaffin cells.

9. The method of claim 8, wherein said means of improving the viability comprises the step of incubating said cells in a culture medium for a short period of time prior to administration.

10. The method of claim 9, wherein said period of time is 7 to 21 days.

11. The method of claim 9, further including the step of testing the improved viability of said cells by ascertaining the production of neuroactive substances secreted by said cells.

12. The method of claim 11, further including the step of administering an immunosuppressant to said patient after administration of said cells.

13. The method of claim 12, wherein said immunosuppressant is Cyclosporin A.

14. The method of claim 1, wherein said chronic pain is of nociceptive origin.

15. The method of claim 1, wherein said chronic pain is of somatic origin.

16. The method of claim 1, wherein said chronic pain is of visceral origin.

17. The method of claim 1, wherein said chronic pain is of neuropathic origin.

18. The method of claim 1, wherein said chronic pain is of central origin.

19. A method of alleviating chronic pain in humans, comprising the step of implanting in a region of the central nervous system of a patient suffering from chronic pain of nociceptive, somatic, visceral, neuropathic or central origin, viable implantable tissue that reduces or eliminates chronic pain without exogenously stimulation of the implanted tissue, wherein the viability of said implantable material is determined prior to implantation by ascertaining the production of a neuroactive substance by said implantable tissue.

20. The method of claim 19, wherein said implantable tissue is maintained in culture for sufficient time to acquire increased viability, wherein the neuroactive substance is chosen from the group consisting of opioid peptides, neurotransmitters and neuropeptides.

21. The method of claim 19 wherein the tissue is adrenal medulla tissue.

22. A method of alleviating chronic pain in a patient, comprising the steps of:
    (a) selecting cells that produce at least one neuroactive substance;
    (b) maintaining the selected cells in vitro for at least seven days to improve viability and neuroactive substance production;

(c) testing for the production of neuroactive substances to prove that the selected cells are viable cells; and (d) introducing the viable cells into a region of the central nervous system of a patient who is suffering from chronic pain, to produce sufficient mounts of at least one neuroactive substance to alleviate chronic pain in the patient without the administration of exogenous stimuli.

23. The method of claim 22 wherein at least one neuroactive substance is a neuropeptide.

24. The method of claim 22 wherein at least one neuroactive substance is met-enkephalin.

25. The method of claim 22 wherein the region of the central nervous system is the subarachnoid space.

26. The method of claim 25 wherein the selected cells are a genetically engineered cell line.

27. The method of claim 26 wherein the selected cells contain recombinant DNA encoding the production of a neuroactive substance.

28. The method of claim 22 wherein the selected cells are human cells.

29. The method of claim 22 wherein the selected cells are heterologous cells.

30. The method of claim 27 wherein the recombinant DNA comprises a nucleotide sequence encoding at least one neuroactive substance chosen from the group consisting of opioid peptides, neurotransmitters and neuropeptides.

31. The method of claim 22 wherein the selected cells are adrenal medullary tissue cells.

32. The method of claim 30 wherein the cells contain recombinant DNA comprising a nucleotide sequence encoding met-enkephalin.

33. The method of claim 22 wherein sufficient numbers of viable cells are introduced to raise the level of at least one neuroactive substance chosen from the group consisting of opioid peptides, neurotransmitters and neuropeptides in the patient's cerebrospinal fluid to a level associated with the relief of chronic pain.

34. The method of claim 33 wherein sufficient numbers of viable cells are introduced to raise the level of met-enkephalin in the patient's cerebrospinal fluid to at least twice the level of the pre-introduction baseline level of met-enkephalin.

35. The method of claim 33 wherein the neuroactive substance is a catecholamine.

36. The method of claim 33 wherein the neuroactive substance is neuropeptide Y.

37. A method of alleviating chronic pain in a patient, comprising the steps of:

(a) selecting genetically engineered cells that produce at least one neuroactive substance;

(b) maintaining the selected cells in vitro to improve viability and neuroactive substance production;

(c) testing the production of neuroactive substances to prove that the selected cells are viable cells; and (d) introducing the viable cells into a region of the central nervous system of a patient who is suffering from chronic pain, to produce sufficient neuroactive substance to alleviate .chronic pain in the patient without administration of exogenous stimuli.

38. The method of claim 37 wherein the selected genetically engineered cells contain recombinant DNA encoding the production of at least one neuroactive substance.

39. The method of claim 37 wherein the recombinant DNA comprises a nucleotide sequence encoding at least one neuroactive substance chosen from the group consisting of opioid peptides, neurotransmitters and neuropeptides.

40. The method of claim 37 wherein the selected genetically engineered cells are PC12 cells containing recombinant DNA encoding the production of human met-enkephalin.

41. The method of claim 37 wherein the selected genetically engineered cells are AtT-20 cells containing recombinant DNA encoding the production of human met-enkephalin.

42. The method of claim 37 wherein sufficient numbers of viable cells are introduced to raise the level of met-enkephalin in the patient's cerebrospinal fluid to at least twice the level of the pre-introduction baseline level of met-enkephalin.

* * * * *